(12) United States Patent
Abad Belando

(10) Patent No.: US 10,537,457 B2
(45) Date of Patent: Jan. 21, 2020

(54) DEVICE FOR INSERTING AN INFLATABLE BALLOON

(71) Applicant: Ramon Abad Belando, Barcelona (ES)

(72) Inventor: Ramon Abad Belando, Barcelona (ES)

( * ) Notice: Subject to any disclaimer, the term of this patent is extended or adjusted under 35 U.S.C. 154(b) by 263 days.

(21) Appl. No.: 15/512,521

(22) PCT Filed: Apr. 23, 2015

(86) PCT No.: PCT/ES2015/070342
§ 371 (c)(1),
(2) Date: Mar. 17, 2017

(87) PCT Pub. No.: WO2016/046427
PCT Pub. Date: Mar. 31, 2016

(65) Prior Publication Data
US 2017/0290694 A1    Oct. 12, 2017

(30) Foreign Application Priority Data
Sep. 26, 2014   (ES) .................................. 201431411

(51) Int. Cl.
*A61F 5/00*   (2006.01)
(52) U.S. Cl.
CPC ............ *A61F 5/0089* (2013.01); *A61F 5/003* (2013.01); *A61F 5/0036* (2013.01)
(58) Field of Classification Search
CPC ...... A61F 5/0089; A61F 5/003; A61F 5/0036; A61F 5/0013; A61M 31/00; A61M 2025/0008; A61M 2025/018; A61M 29/00
See application file for complete search history.

(56) References Cited

U.S. PATENT DOCUMENTS

| 4,485,805 A | 12/1984 | Foster, Jr. | |
| 5,391,159 A * | 2/1995 | Hirsch | A61J 15/0019 604/175 |
| 2012/0172895 A1* | 7/2012 | Fridez | A61B 17/3468 606/139 |
| 2014/0236129 A1 | 8/2014 | Radl | |

FOREIGN PATENT DOCUMENTS

| WO | 2011/041864 A1 | 4/2011 |
| WO | 2012/089881 A1 | 7/2012 |

* cited by examiner

*Primary Examiner* — Katrina M Stransky
(74) *Attorney, Agent, or Firm* — Knobbe, Martens, Olson & Bear, LLP

(57) ABSTRACT

The invention relates to a device for inserting an inflatable balloon which comprises a main body of revolution (12) which defines a cone-shaped distal end and a proximal end, said main body also comprising: a first internal channel (123) passing from the proximal end to the distal end of said body for inserting a thread (3) for guiding said device; an internal compartment (125) arranged in a portion of the distal end of said body for housing an inflatable balloon (4), said compartment comprising a breakable outer surface (1251) which is continuous with the surface of said body, and a second internal channel passing from the distal end of said body to said compartment, for housing a balloon inflation tube (5) suitable for connection at the distal end thereof with an inflatable balloon inside said compartment.

17 Claims, 10 Drawing Sheets

DEVICE FOR INSERTING AN INFLATABLE BALLOON

CROSS-REFERENCE TO RELATED APPLICATIONS

This application is the U.S. National Phase under 35 U.S.C. § 371 of International Application PCT/ES2015/070342, filed Apr. 23, 2015, which claims priority to Spanish Patent Application No. P201431411, filed Sep. 26, 2014. The disclosures of the above-described applications are hereby incorporated by reference in their entirety.

FIELD OF THE INVENTION

The present invention relates to a device for inserting an inflatable balloon used for the treatment of obesity.

In particular, the present invention relates to a device that allows an inflatable balloon (also known as a "gastric balloon") to be implanted temporarily in the stomach of patients with obesity and which helps achieve significant weight loss in a short period of time.

BACKGROUND OF THE INVENTION

Treatment using intragastric balloons was introduced in the mid 1990s, being proposed as an attractive weight-loss option for patients who did not respond to medical therapy and who did not wish or should not undergo a surgical operation or drug treatment.

Said treatment comprises the use of a deflated inflatable balloon connected to the distal end of a tube for inflating or feeding the balloon which is inserted blind through the patient's mouth and passes through the oesophagus until it reaches the stomach. The balloon inflation tube must be long enough for the proximal end of said inflation tube to remain outside the patient. Once the deflated balloon is in the stomach, a syringe is inserted through the orifice at the proximal end of said inflation tube which projects from the patient's mouth and a liquid or air is introduced which inflates the balloon inside the stomach. Once the balloon is inflated in the stomach, the inflated balloon is released from the distal end of said inflation tube and said inflation tube is then removed from inside the body of the patient.

However, the process of placing the balloon, using known techniques, is carried out blind by touch and it is not possible to monitor where the balloon connected to the inflation tube is passing along. In some cases, said technique has led to incorrect insertion of the balloon causing injury to the oropharynx, larynx or trachea. To prevent incorrect insertion of the balloon via the trachea, in some cases the patient is intubated beforehand via the trachea to secure the airway and the balloon is then inserted connected to the inflation tube. However, the use of a respiratory probe requires more control than is necessary for inserting the balloon, causes the patient discomfort afterwards and does not ensure correct insertion of the balloon thus avoiding injuries.

An example of a device for inserting a gastric balloon is disclosed in patent application PCT WO 2012/089881. Said application discloses a device which is made up of a guide tube with a conical distal end connected adjacent to the inflation tube which in turn is connected to an inflatable balloon. The guide tube comprises an internal through-hole from the proximal end to the distal end for inserting a pre-guiding thread. Said thread is inserted in the patient's stomach beforehand and forms a pathway along which the guide tube is inserted together with the inflation tube and the inflatable balloon inside the stomach.

Although the device of application PCT WO 2012/089881 discloses an improvement for guiding the inflation tube connected to the balloon towards the stomach, there is still a risk that the inflation tube may become detached from the guide tube or even from the balloon due to rubbing on the oesophagus wall.

In addition, with this type of device comprising a pre-guiding thread which serves as a pathway for inserting the device and is inserted initially through the patient's oesophagus in a first step, the flexible nature of said thread means that often it forms kinks on the oesophagus wall. When this happens, and after the doctor has inserted the guide tube along said thread inside the patient, the conical distal end of said guide tube often becomes stuck at the point of said wall where said pre-guiding thread has formed a kink, as shown in FIG. 1, and can cause serious injuries to the oesophagus wall and may even lead to the perforation of said wall, most particularly in patients with diverticula in this route.

Moreover, both with this type of device and other devices of the prior art for inserting gastric balloons, the method used to release the inflated balloon inside the stomach usually takes place aided by the anatomical structure of the cardia (that is, the portion of the stomach next to the oesophagus). When the inflation tube is pulled out of the body of the patient, the cardia forms a stop for the inflated balloon, releasing the connection between the inflation tube and the inflated balloon, said inflated balloon being left free inside the stomach. However, in many cases this widespread practice causes serious damage and injuries to the cardia which, particularly in obese patients and above all in cases of morbid obesity, can cause internal bleeding that is difficult to stop or even, irreparable injuries especially in patients with a hiatus hernia.

An object of the present invention is therefore to produce a device for inserting a gastric balloon that allows said drawbacks to be overcome. More particularly, an object of the present invention is to disclose a device for inserting a gastric balloon which ensures correct insertion of the gastric balloon as far as the stomach, preventing said gastric balloon from being undesirably diverted towards other structures, and eliminating the risk of perforation and internal bleeding of the oropharynx, the airways or injuries to the stomach or the cardia. A further object of the present invention is to disclose a compact and efficient device that prevents the balloon from being released or detached or unhooked inopportunely and in addition does not use the assistance of the internal organs when the inflated balloon is to be released inside the stomach.

SUMMARY OF THE INVENTION

According to the present invention, this is achieved by means of a device for inserting an inflatable balloon of the type that uses a thread for the guidance thereof characterised in that it comprises a main body of revolution which defines a cone-shaped distal end and a proximal end, said main body also comprising:
  a first internal channel passing from the proximal end to the distal end of said body for the insertion of a thread for guiding said device;
  an internal compartment arranged in a portion of the distal end of said body for housing an inflatable balloon, said compartment comprising a breakable outer surface continuous with the surface of said body, a second internal channel passing from the proximal end of said body to said compartment, for housing a balloon inflation tube, said inflation tube being adapted for its connection by the distal end thereof with an inflatable balloon inside said compartment, and a distal end of said body finishing in a head with a flexible neck through which said first internal channel extends.

Thus, when said device is inserted inside the oesophagus, guided by the guide thread, the head with a flexible neck allows the device to be gently redirected if there are kinks in said guide thread, thus preventing injuries and even perforations as said device travels along the anatomical walls of the oropharynx, oesophagus and stomach.

According to a first embodiment of the invention, said device for inserting an inflatable balloon comprises a main closed body of revolution which defines a proximal end and a cone-shaped distal end. Said main body also comprises a first internal channel passing from the proximal end to the distal end of said body for inserting a thread for guiding said device. In addition, according to this first embodiment of the invention, said main body also comprises an internal compartment which is arranged in a portion of the distal end of said body and in which an already incorporated inflatable balloon is housed, said compartment comprising a breakable outer surface which is continuous with the surface of said body. Furthermore, according to this first embodiment of the invention, said main body also has a second internal channel passing from the proximal end of said body to said compartment, in which the already incorporated balloon inflation tube is housed and which is suitable for connection by the distal end thereof with said inflatable balloon already incorporated inside said compartment. Finally, the distal end of said body finishes in a head with a flexible neck through which said first internal channel extends.

According to a second embodiment of the invention, said device for inserting an inflatable balloon also comprises a main body of revolution which defines a proximal end and a cone-shaped distal end finishing in a head with a flexible neck, said main body further comprising a first internal channel passing from the proximal end to the end of said body with the head for inserting a thread for guiding said device. In addition, according to this second embodiment of the invention, said main body also comprises an internal compartment arranged in a portion of the distal end of said body for housing an inflatable balloon, said compartment comprising an outer breakable surface continuous with the surface of said body. Moreover, according to this second embodiment of the invention, said main body also comprises a second internal channel passing from the proximal end of said body to said compartment, for housing a balloon inflation tube suitable for connection by the distal end thereof with an inflatable balloon inside said compartment. In this second embodiment, the main body also comprises a resilient longitudinal opening for access to said second internal channel, arranged on the surface thereof between the proximal end of said body and the compartment, said opening being suitable for inserting any inflatable balloon which is commercially available and/or of the prior art inside the compartment connected to any inflation tube of the prior art, said inflation tube being incorporated in said second channel. Owing to its resilience, said opening opens for placing the inflation tube in said second channel and the inflatable balloon connected to said inflation tube inside the compartment. After placing the inflation tube and the inflatable balloon, said opening, owing to its resilience, returns to its initial position thus preventing said inflation tube from being able to escape from the second internal channel of the main body. This second embodiment therefore allows any commercially available inflatable balloon together with the corresponding inflation tube to be inserted in the main body of the device.

Both the first and second embodiments of said device comprise in one body all the basic elements for correct insertion of an inflatable balloon inside the stomach, considerably enhancing the safety precautions for the patient. Furthermore, as the inflatable balloon is enclosed in the internal compartment, there is no risk of it becoming detached too soon while the device is being inserted. Nor is there a risk with this device of the balloon inflating completely or in part in an unsuitable place.

In addition, the device according to the first and second embodiments allows the inflatable balloon to be placed inside the stomach with the intervention of only a medical specialist, that is, with no need for any medical assistant, nurse and/or nursing auxiliary.

Preferably, in both the first and second embodiments of the present invention, said first internal channel is arranged inside the main body along the central longitudinal axis of said body. The device can therefore be guided by a guide thread which traces a path along said first internal channel.

Also preferably, in both the first and second embodiments of the present invention, said second internal channel is arranged along a longitudinal axis that is not concentric with the central axis of said body.

Preferably, in both the first and second embodiments of the present invention, the head arranged in continuation of the distal end of the main body is ogive-shaped with a rounded point. Thus, if the pre-guiding thread becomes kinked at some point of the oesophagus wall, the ogive-shaped head with a rounded point allows the device to be redirected, thus avoiding damage and/or perforations in the oesophagus wall and the walls of other anatomical organs on the path of the device, such as the walls of the oropharynx and the stomach, for example.

Preferably, in both the first and second embodiments of the present invention, the internal compartment for housing the inflatable balloon comprises a base truncated along a longitudinal plane parallel to the central axis of the body which does not pass through the centre of the main body.

Preferably, the distal end of said main body is more slender and more flexible than the proximal end of the body.

Preferably, in both the first and second embodiments of the present invention, the length of said main body is less than the thread used to guide said device and less than the inflation tube of the inflatable balloon.

Preferably, in both the first and second embodiments of the present invention, the connection between the distal end of the inflation tube and the inflatable balloon is detachable. In addition, the inflatable balloon comprises a non-return valve, and therefore, once the balloon is inflated, either by air or by serum, no leaks can escape through said valve.

Preferably, in both the first and second embodiments of the present invention, the thread for guiding said device and the inflation tube of the inflatable balloon are of the flexible resilient type.

Preferably, in both the first and second embodiments of the present invention, said main body also comprises double length marking along its surface to indicate the location of the head of the main body and the proximal end of the inflatable balloon during insertion of the device inside the patient's stomach. Thus, the distance of the head of the main body and the inflatable balloon is known at all times.

BRIEF DESCRIPTION OF THE DRAWINGS

For a better understanding of the invention, the accompanying drawings provide an explanatory but non-limiting example describing the various parts of a preferred embodiment of the present invention.

DETAILED DESCRIPTION OF THE PREFERRED EMBODIMENTS

Figure 2:
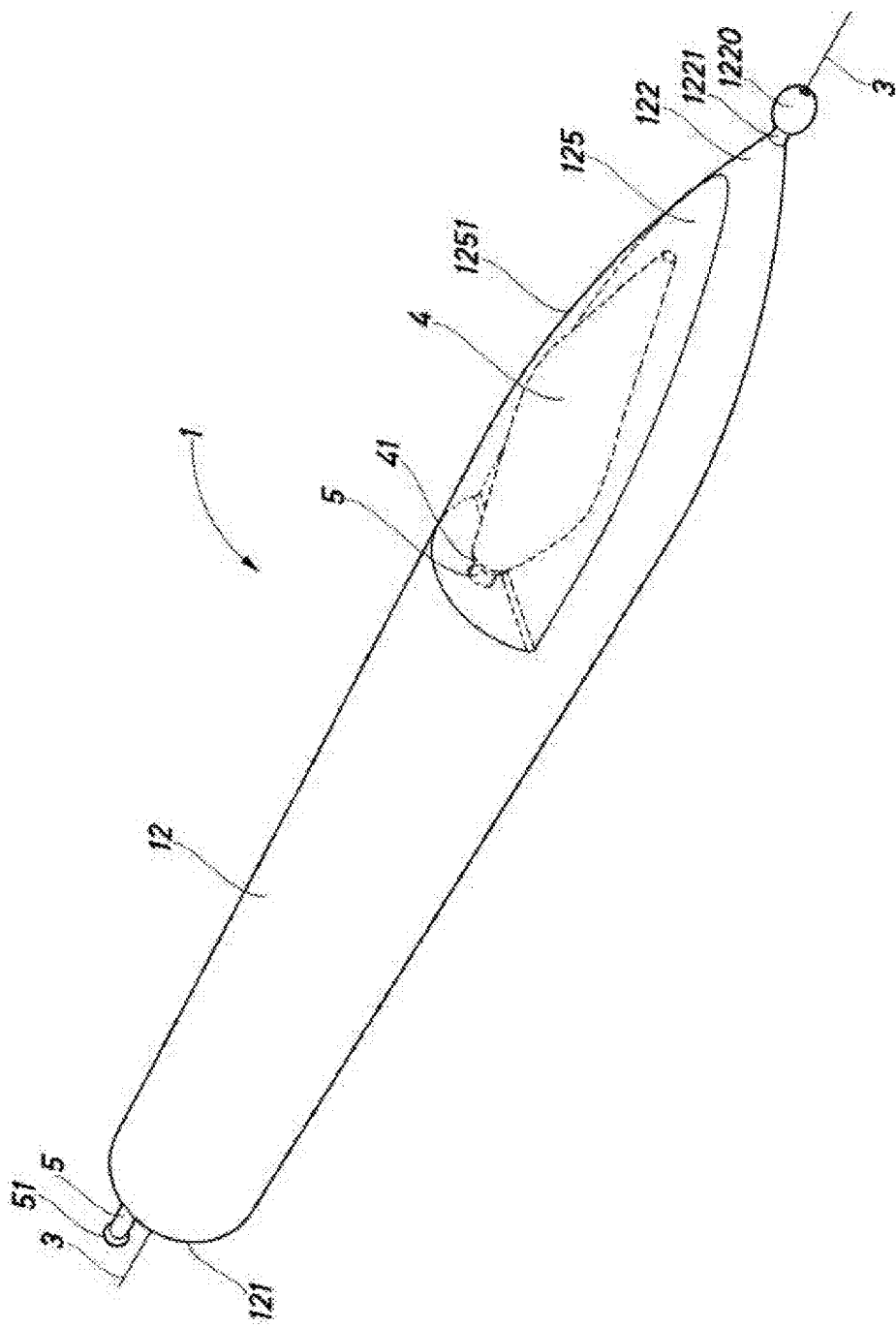
FIG. 2 is a perspective view of a first embodiment of a device for inserting an inflatable balloon according to the present invention.
Figure 3:
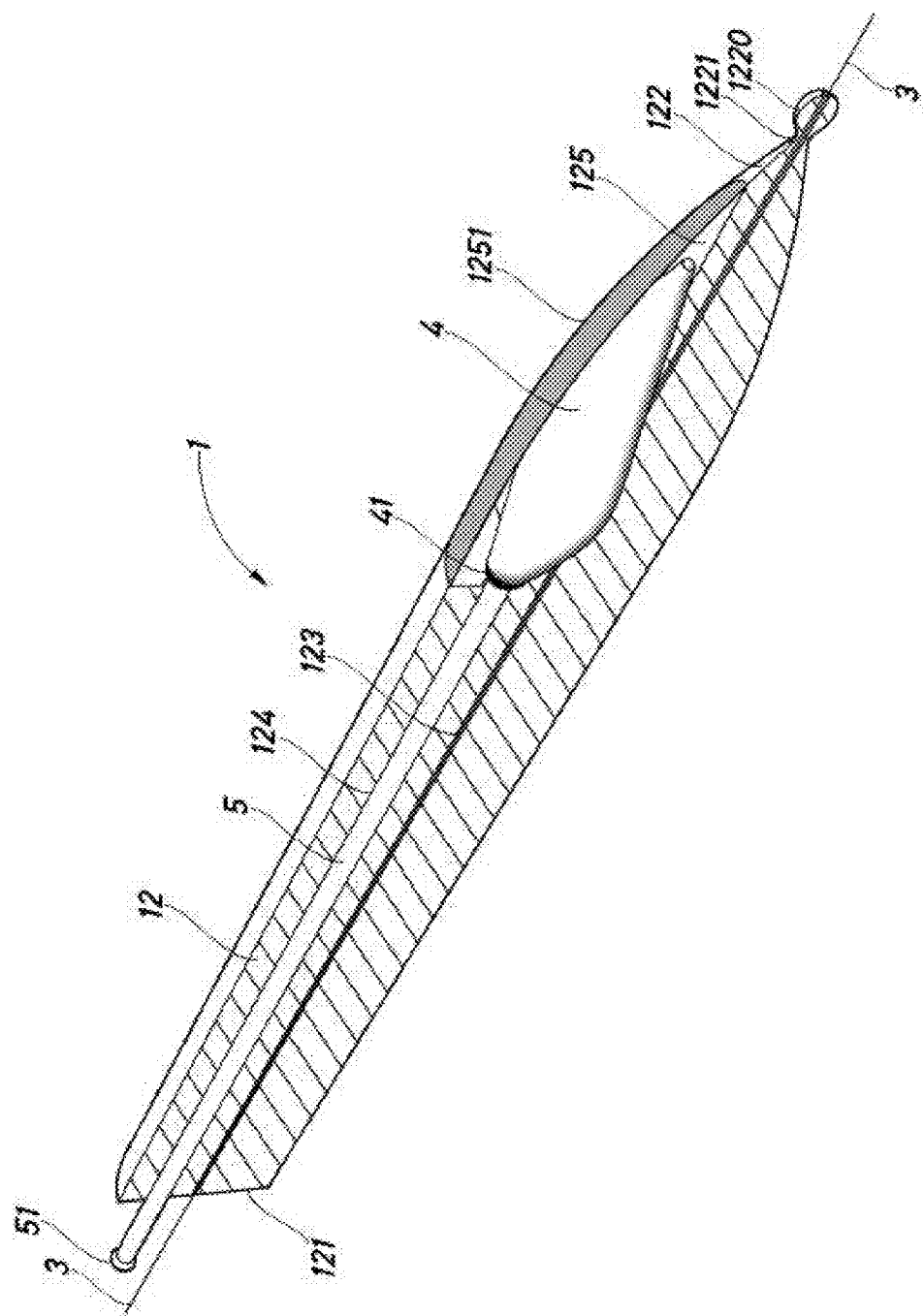
FIG. 3 is a perspective view in longitudinal cross section of the first embodiment of the device for inserting an inflatable balloon of FIG. 1.

FIGS. 2 and 3 show a device -1- for inserting an inflatable balloon (also known as a "gastric balloon), according to a first embodiment of the present invention, which comprises a main body of revolution -12- which defines a proximal end -121- and a cone-shaped distal end -122- finishing with a head -1220- with a flexible neck -1221-. Said main body -12- also comprises a first internal channel -123- passing from the proximal end -121- to the distal end of the head -1220- of said body -12- for inserting a thread -3- for guiding said device -1- also known as the "pre-guiding thread". In addition, according to this first embodiment of the present invention, said main body -12- also comprises an internal compartment -125- arranged in a portion of the distal end -122- of said main body -12- for housing an inflatable balloon -4-. Said compartment -125- comprises a breakable outer surface -1251- which in addition is continuous with the unbreakable surface of said main body -12-. Furthermore, the surface -1251- of said compartment -125- can be smooth and soft to avoid causing injury to the walls of the organs where said surface passes. However, said surface -1251- can at the same time be very easily broken when subjected to minimal inflation pressure from the balloon -4-.

Furthermore, according to this first embodiment of the invention, said main body -12- also comprises a second internal channel -124- passing from the proximal end -121- of said main body -12- to the proximal end of said internal compartment -125-, for housing a balloon inflation tube -5- suitable for connection at the distal end thereof with said inflatable balloon -4- incorporated inside said compartment -125-.

It is recommended that the main body -12- should have a minimum length of 100 centimetres so that at least the head -1220- and the compartment -125- of the body -12- can be inserted as far as the patient's stomach, while maintaining a substantial portion of the proximal end -121- of the device -1- outside the patient's mouth and to thus be able to implement the method of inserting the balloon -4- into the stomach of said patient. It is also important that the diameter of the entire main body -12- should at the same time allow a conventional endoscope to be inserted in order to check the patient's oesophagus, stomach and duodenum visually before, during and after the procedure for inserting the device -1-.

In addition, said first internal channel -123- is arranged inside the main body -12- along the central longitudinal axis of said body -12-. In this way, the device -1- can be guided more easily owing to said guide thread -3-, inserted in an earlier step as far as the patient's stomach. Said thread -3-, which is usually inserted in an earlier step through the patient's oesophagus as far as the stomach and duodenum, is preferably flexible and smooth so as not to damage the walls of the oesophagus, stomach and duodenum. In addition, said thread -3- may be made of different materials such as metal, nitinol, hard nylon, etc. Also, said thread -3- might have a diameter of approximately 1.2 mm and an approximate length of 4 metres, longer than the approximately 100 cm of the main body -12-, so that it can be inserted before the main body -12- and then serve as a guide along said first internal channel -123-.

In addition, said second internal channel -124- is arranged inside the main body -12- along a longitudinal axis that is not concentric with the central axis of said body -12-, being capable to house a balloon inflation tube -5-, also known as a balloon feed probe. Said inflation tube -5-, which according to this first embodiment can be incorporated inside said second internal channel -124- of the main body -12-, may have an approximate diameter of 3 to 4 mm and may be longer than the 100 cm length of the main body -12-, so that the proximal end -51- of said balloon inflation tube -5- can remain outside the patient's mouth while a portion of the main body -12- is inserted inside the patient.

Moreover, the inflatable balloon -4-, which according to this first embodiment may also be incorporated inside the internal compartment -125- of the main body -12- of the device -1-, is approximately 8 to 10 millimetres in diameter and is fully collapsed inside the compartment -125-, which is some 8-10 centimetres long, before being inflated. Said inflatable balloon -4- is connected to the distal end of said inflation tube -5- by means of a detachable connection of a type known in the prior art. In addition, the portion of the balloon -4- that is initially connected to the inflation tube -5- comprises a non-return valve -41-, also known as one-way valves or check valves. The object of this type of valve is to allow a fluid, which may be a gas or a liquid, to flow only in one direction and to completely close the passage of said fluid in the opposite direction. Thus, said non-return valve -41- allows fluid to pass into, but not out of the balloon -4-. Moreover, when the inflation tube -5- and the non-return valve -41- of the balloon -4- separate, said non-return valve -41- closes automatically.

Figure 4:
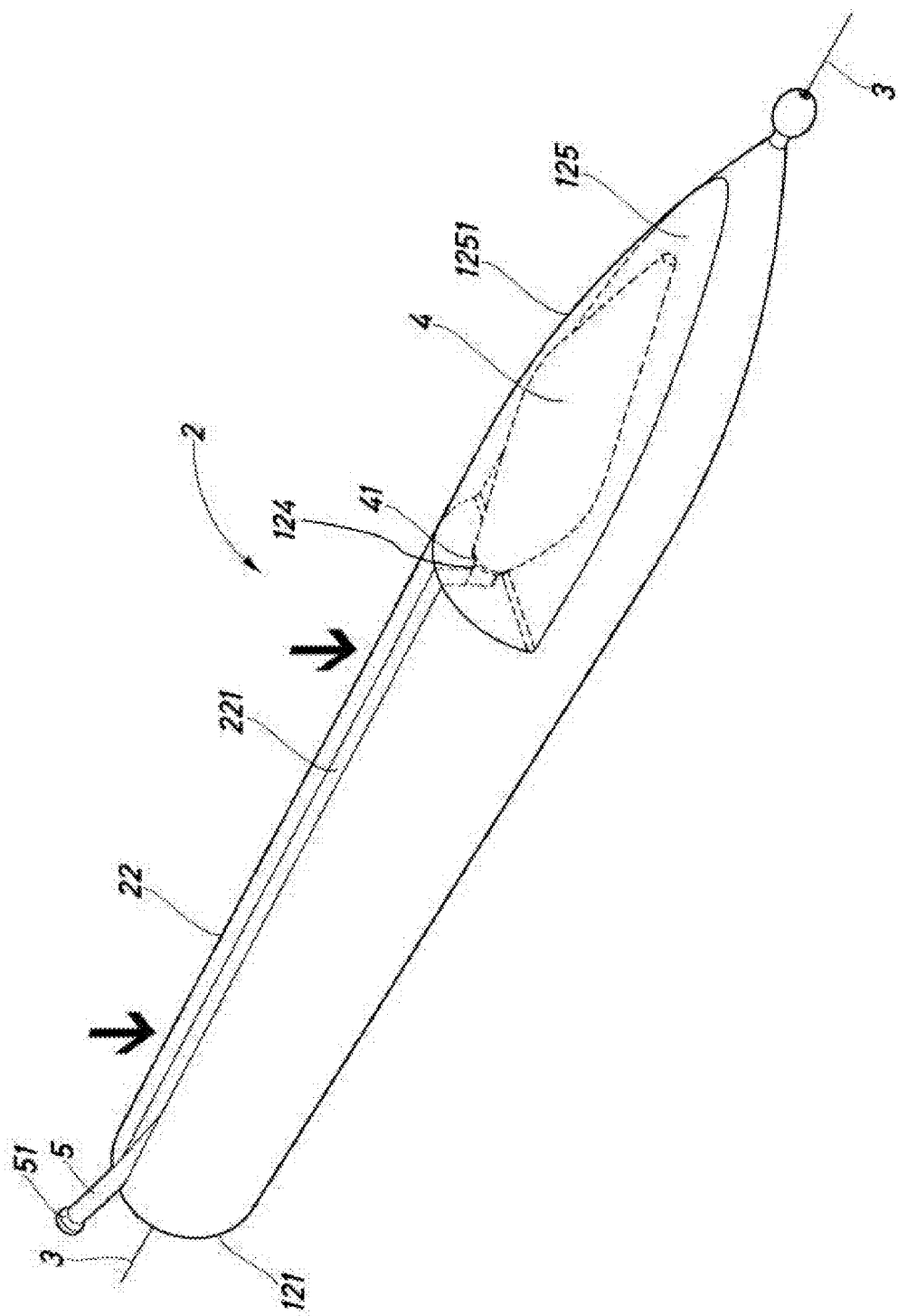
FIG. 4 is a perspective view of a second embodiment of a device for inserting an inflatable balloon according to the present invention.

FIG. 4 shows a device -2- for inserting an inflatable balloon, according to a second embodiment of the present invention, which comprises similar technical features to those of the first embodiment of the device -1-. However, the device -2- of said second embodiment comprises a main body -22- which also comprises a resilient longitudinal opening -221- for access to the second internal channel -124-. Said resilient longitudinal opening -221- is arranged on the surface of the main body -22- between the proximal end -121- of the main body -22- and the proximal end of the internal compartment -125-. In this way, the device -2- allows any commercially available assembly (inflation tube -5- connected to an inflatable balloon -4-) to be inserted. Said longitudinal opening -221- is resilient and, consequently, can be opened and extended far enough to insert and place the inflation tube -5- in the second channel -124- and the inflatable balloon -4- (connected to said inflation tube -5-) inside the internal compartment -125- respectively. After placing the assembly (inflation tube -5- connected to an inflatable balloon -4-), said opening -221-, returns to its initial natural position, owing to its resilience, preventing said inflation tube -5- from being able to escape from the second internal channel -124- of the main body. In this way, according to this second embodiment, any commercially available inflatable balloon together with the corresponding inflation tube can be inserted in the device -2-.

In general, the commercially available inflatable balloons are made of a very strong plastics material which, once inflated and released inside the stomach, have a service life of 6 to 8 months.

In addition, in both the first and second embodiments of the present invention, said main body (-12-, -22-) also comprises a double length marking (not shown) along its surface to indicate the location of the head -1220- of the main body (-12-, -22-) and the proximal end of the inflatable balloon -4- during insertion of the main body (-12-, -22-) inside the patient's stomach. The markings may be different colours to define risk and safety zones.

According to a method of using a device (-1-, -2-) for inserting a gastric balloon according to the present invention, in a first phase (not shown) it is usually advisable, before placing a balloon in a patient's stomach, to carry out a routine but exhaustive exploration of the oesophagus, stomach and duodenum to ensure that there are no injuries that could contraindicate the gastric balloon treatment. Thus, in a first phase (not shown) an endoscopic device is inserted, which comprises a proximal end and a distal end, through the patient's mouth until it reaches the patient's duodenum, such that the distal end of said endoscopic device is located at the start of the duodenum and the proximal end thereof is outside the patient's mouth. Said endoscopic device makes it possible to check that no counterproductive anomaly exists.

Said endoscopic device may comprise at least a channel through which the pre-guiding thread -3- is inserted until it reaches the duodenum so that the distal end of said pre-guiding thread -3- is arranged at the start of the duodenum and the proximal end of the same thread -3- is outside the patient's mouth. The endoscopic device thus serves as a guide for said pre-guiding thread -3- as far as the duodenum, ensuring correct insertion thereof.

The endoscopic device is then removed leaving the pre-guiding thread -3- with its proximal end outside the patient and the distal end of said thread -3- at the start of the duodenum. As indicated earlier in the description, the pre-guiding thread -3- must be made of a suitably soft material such as nitinol to avoid damaging the mucous membranes of the oesophagus, stomach and duodenum. Optionally, the pre-guiding thread -3- can be pushed inside the patient while at the same time removing the endoscopic device.

Finally, at the end of this first initial step (not shown), the pre-guiding thread -3- is correctly positioned between the start of the duodenum, through the stomach, oesophagus, oropharynx and the outside of the patient's mouth.

Next, in a second step (not shown), the main body (-12-, -22-) of the device (-1-, -2-) is inserted through the patient's mouth ensuring that the distal end of the head -1220- of the main body (-12-, -22-) coincides with the proximal end of the pre-guiding thread -3- which remains outside the patient. Next, the main body (-12-, -22-) is pushed on the guide thread -3- through the patient's oropharynx, oesophagus and finally stomach. During this step, the pre-guiding thread -3- ensures that the main body (-12-, -22-) does not move to the airways and the flexibility of the main body (-12-, -22-) allows it to adapt to the anatomical structures (oropharynx, oesophagus, stomach, duodenum). In addition, the absence of external fasteners and attachment mechanisms between the main body (-12-, -22-) and the assembly (inflation tube -5- connected to an inflatable balloon -4-) prevents injuries through rubbing or possible detachment.

Figure 1:
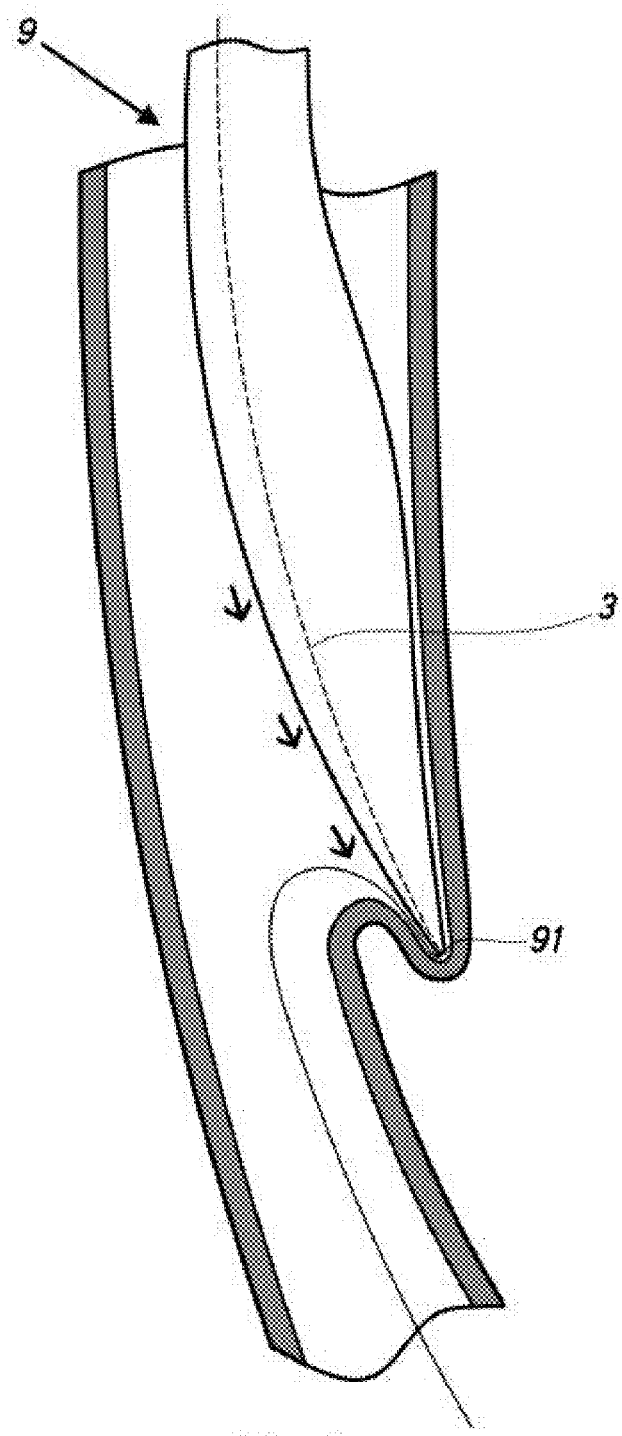
FIG. 1 is a side view in longitudinal cross section of a device from the prior art for inserting an inflatable balloon with the conical distal end pricking a portion of the oesophagus wall during the insertion of said device inside the oesophagus.
Figure 8:
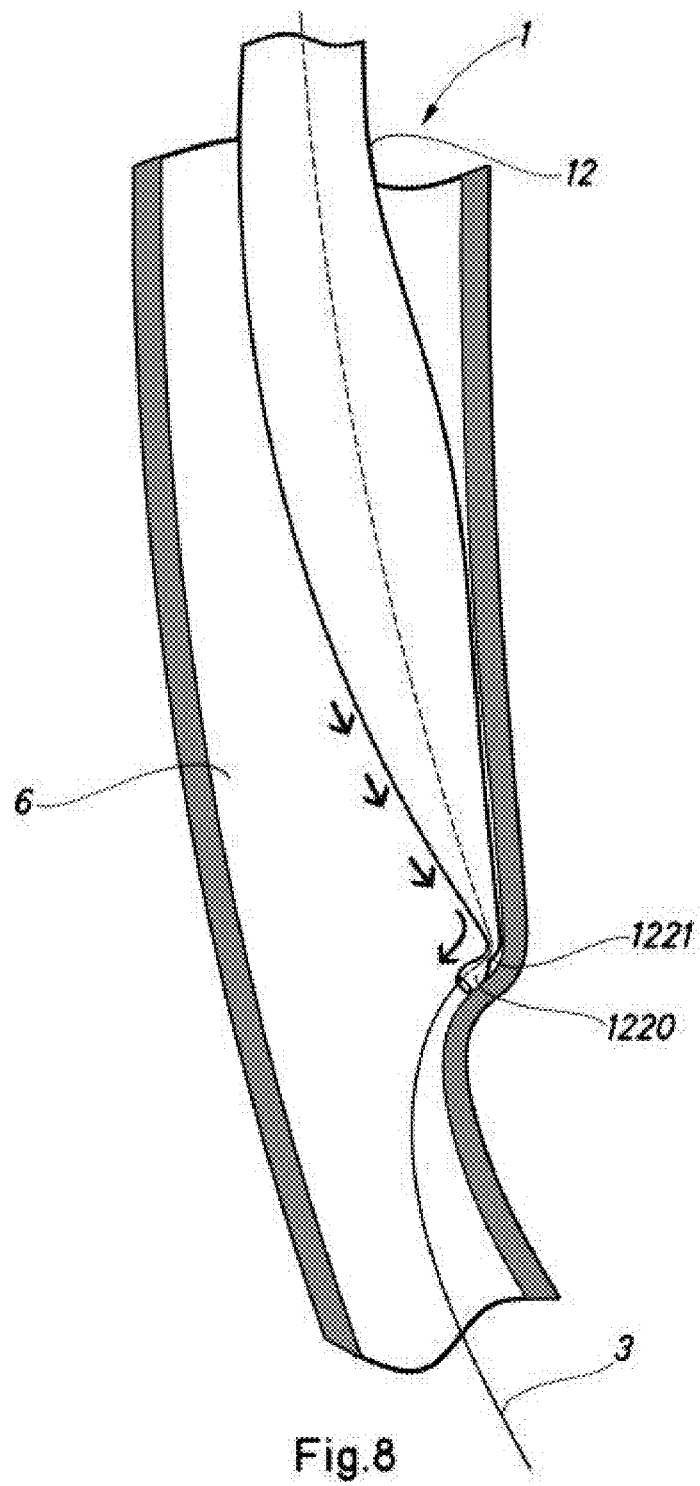
FIG. 8 is a side view in longitudinal cross section of a device for inserting an inflatable balloon according to the present invention with the conical distal end finished by a head with a flexible neck which redirects the trajectory of the device after encountering a kink in the guide thread in the oesophagus wall while inserting said device inside the oesophagus.
Figure 9:
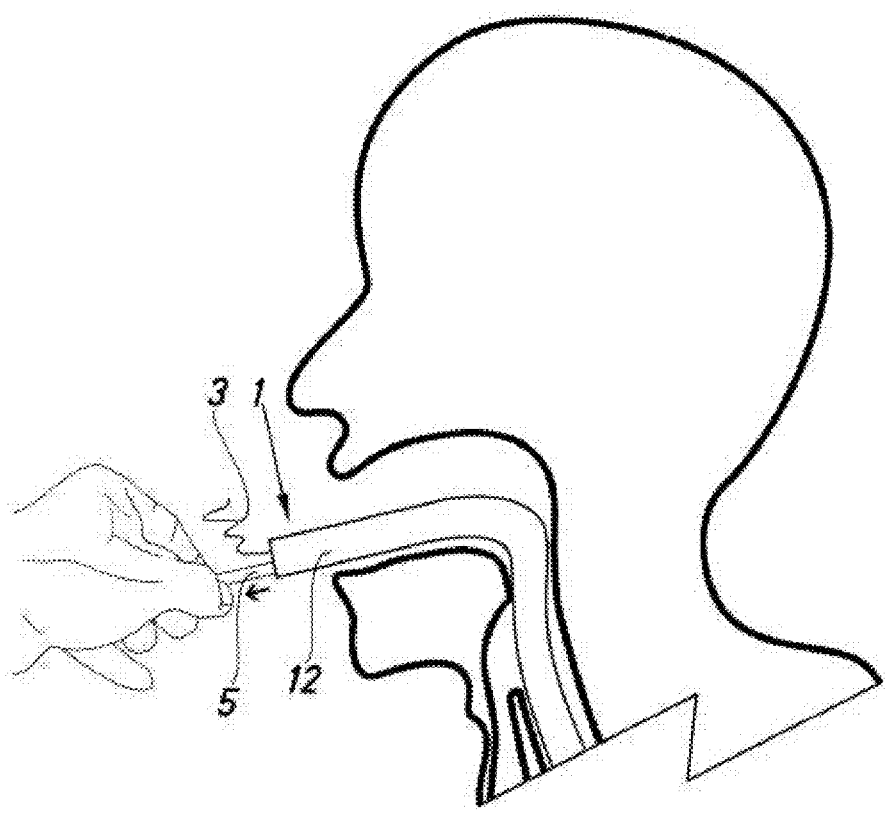
FIG. 9 is an elevation diagrammatic view of the step in the method of inserting an inflatable balloon in which the inflated balloon becomes detached from the inflation tube as the inflation tube is pulled out of the patient's stomach.
Figure 9:
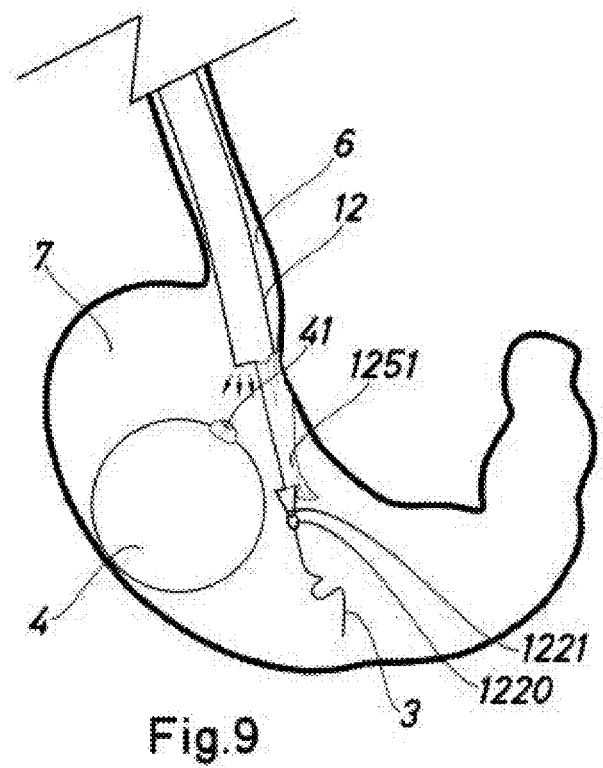

During this second step, should the thread -3- have become kinked at any point of its travel (oropharynx, oesophagus, stomach, duodenum), the head -1220- with a rounded point and flexible neck -1221- at the distal end of the main body (-12-, -22-), as shown in FIG. 8, helps redirect said main body (-12-, -22-) along its path (oropharynx, oesophagus, stomach, duodenum) thus avoiding possible injury and/or perforation of the walls of the oropharynx or the oesophagus. In many cases, said injuries are generally caused by devices -9- for inserting a gastric balloon of the prior art with a conical distal end -91-, as shown in FIG. 1. Because of their cone-shaped distal end -91- finishing in a point, said devices -9- can become stuck at a point of said wall where said pre-guiding thread -3- has become kinked, which can cause serious injury to the oesophagus wall and may even lead to perforation of said wall.

Finally, the optional length markings (not shown) arranged on the surface of the main body (-12-, -22-) ensure correct positioning of the internal compartment -125- in the stomach -7-.

Figure 5:
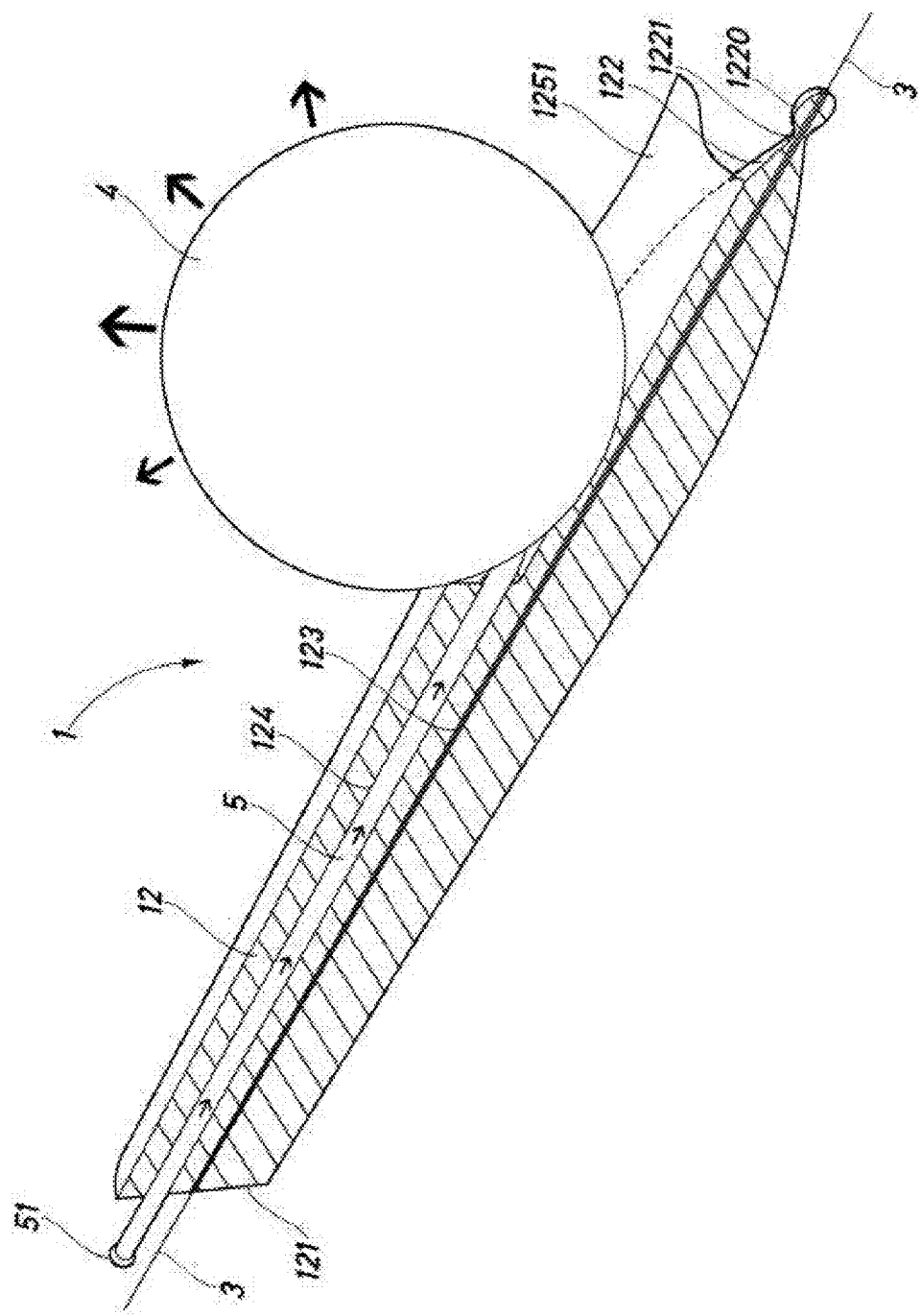
FIG. 5 is a perspective view in longitudinal cross section of the first embodiment of the device for inserting an inflatable balloon, according to a step of a method of using said device in which the inflatable balloon is inflated and causes the breakable surface of the compartment of said device to become detached.
Figure 6:
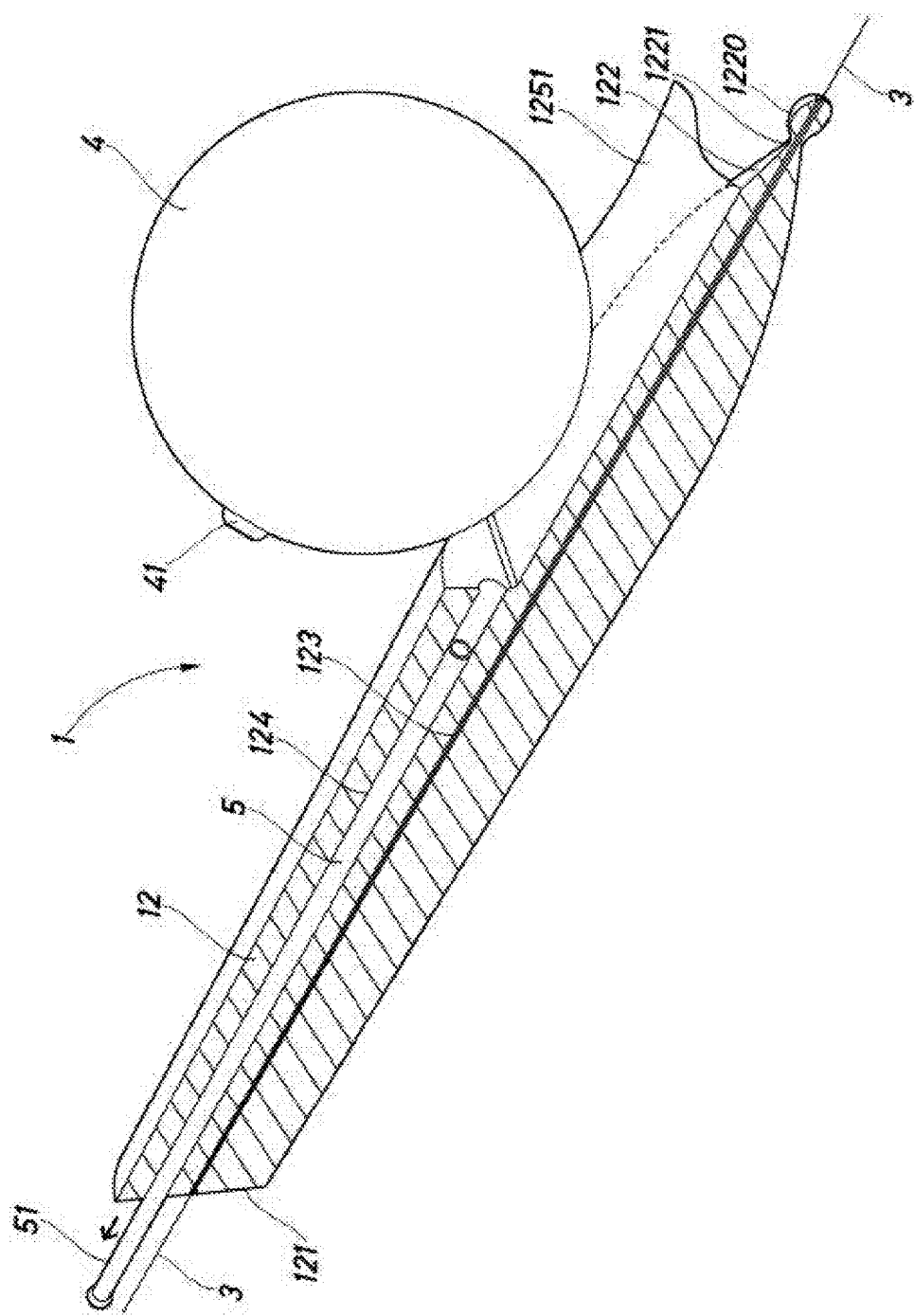
FIG. 6 is a perspective view in longitudinal cross section of a first embodiment of the device for inserting an inflatable balloon, according to another step of a method of using said device in which the inflated gastric balloon becomes detached from the inflation tube.
Figure 7:
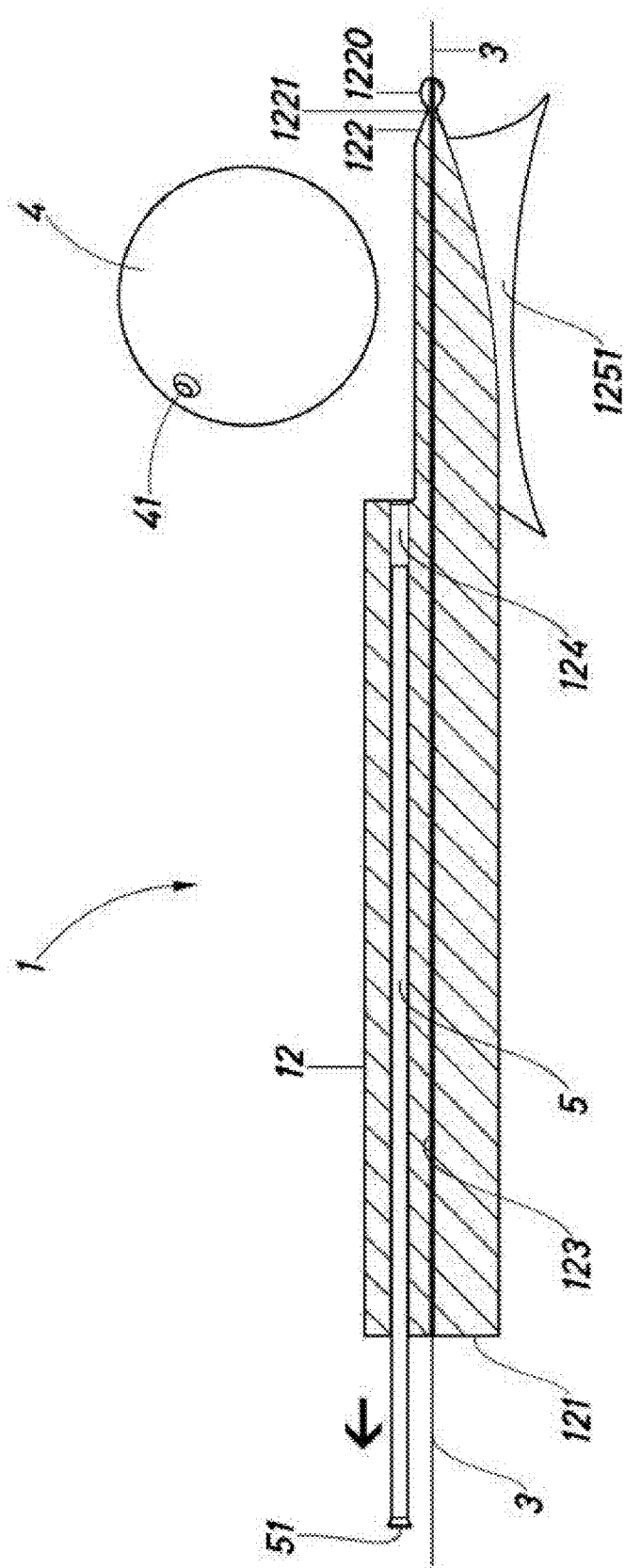
FIG. 7 is a view in elevation and in longitudinal cross section of the first embodiment of the device for inserting an inflatable balloon, according to the same step shown in FIG. 6 of a method of using said device.

Next, in a third step, once the head -1220- and the internal compartment -125- of the main body (-12-, -22-) are positioned in the patient's stomach -7-, the non inflated balloon -4- arranged inside said compartment -125- is inflated. To do this, a liquid (a saline solution such as serum, for example) or alternatively air can be injected through the proximal end -51- of the inflation tube -5- arranged outside the patient's mouth. Both the serum and the air inserted through the inflation tube -5 allow the balloon -4- arranged in the internal compartment -125- to be inflated. As the balloon -4- inflates, the smooth, soft surface -1251- of said internal compartment -125- starts to give way until broken by the inflation pressure of the balloon -4-, as shown in FIG. 5. Although a portion of the detached surface -1251- may remain connected to the surface of the main body (-12-, -22-), another detached portion of said surface -1251- could remain free inside the stomach -7-. Said surface -1251- may be made, for example, of a material that is easily digested by the stomach, leading to the portions of said surface -1251- that have become completely detached from the main body (-12-, -22-) eventually being eliminated from the stomach. Optionally, the diameter of the main body (-12-, -22-) ensures that all these steps can be viewed and monitored by means of an endoscopic device inserted parallel to the main body (-12-, -22-).

Next, in a fourth step, the inflated balloon -4- is released from the connection between said balloon -4- and the inflation tube -5-. To do this, the proximal end -51- of the inflation tube -5- arranged outside the patient's mouth is pulled, causing the connection between said balloon -4- and the inflation tube -5- to come closer to the distal end of the second internal channel -124- of the main body (-12-, -22-). The diameter of the second internal channel -124- through which the inflation tube -5- slides is smaller than the connection between said balloon -4- and the inflation tube -5-. Consequently, the distal end of said second channel -124- forms a stop, when the connection between said balloon -4- and the inflation tube -5- makes contact with said distal end of said second channel -124-, causing the inflated balloon -4- to become detached from the distal end of the inflation tube -5- and, as a result, releases the inflated balloon -4- inside the stomach -7-, as shown in FIGS. 5, 6, 7 and 9. According to this fourth step, a portion of the main body (-12-, -22-) is used as a stop without involving any of the patient's internal organs, and consequently avoiding any kind of internal injury in the patient.

Figure 10:
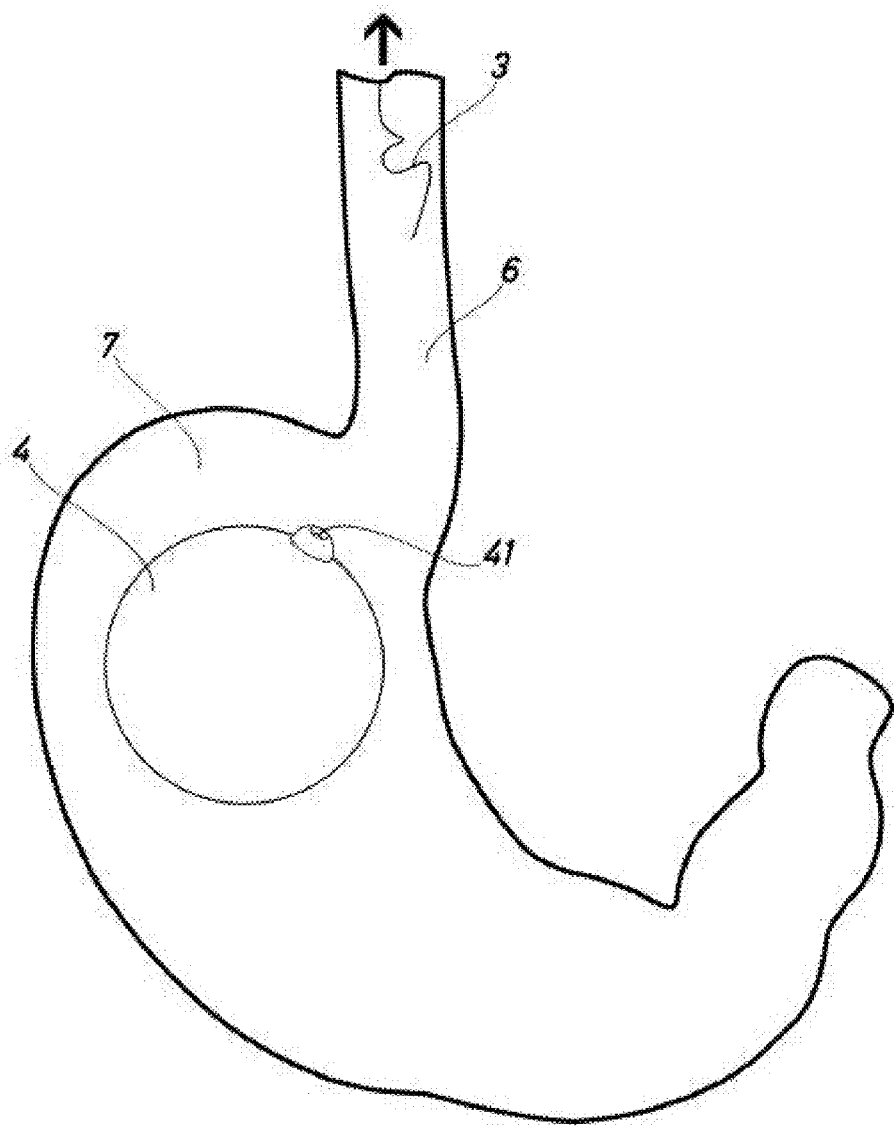
FIG. 10 is a view in elevation of the final step in the method of inserting an inflatable balloon in which, once the device according to the present invention has been removed, the guide thread of said device is extracted.

Once the balloon -4- is inflated and loose inside the stomach -7-, first the main body (-12-, -22-) is removed to the outside, while keeping said pre-guiding thread -3- (not shown) in position. Finally, the pre-guiding thread -3- is removed by pulling said thread gently out of the patient, as shown in FIG. 10. Optionally, the patient's internal anatomical organs can be checked with an endoscopic device to confirm that there are no injuries.

The present invention therefore allows an inflatable balloon to be inserted inside a patient's stomach using a single compact device, with no complications, injury or damage of any kind, eliminating the risk of perforation and/or bleeding of the airways, oropharynx, oesophagus, stomach and duodenum. In addition, with the device (-1-, -2-) according to the present invention, an efficient, rapid (in a few seconds) method of inserting an inflatable balloon is achieved, without the need for an anaesthetic and without the need for the intervention of a medical assistant, nurse and/or medical auxiliary.

Although the invention has been described with respect to a preferred embodiment, this should not be considered as limiting the invention, the scope of which is defined by the widest interpretation of the following claims.

What is claimed is:

1. A device for inserting an inflatable balloon that uses a thread for guidance comprising a main closed body of revolution which defines a cone shaped distal end and a proximal end, wherein said main body comprises:
    a first internal channel passing from the proximal end to the distal end of said body for inserting the thread for guiding said device;
    an internal compartment arranged in a portion of the distal end of said body and in which an inflatable balloon is housed, said compartment comprising a breakable outer surface which is continuous with a surface of said body;
    a second internal channel passing from the proximal end of said body to said compartment in which an inflatable balloon inflation tube is housed, said inflation tube being suitable for connection by the distal end thereof with said inflatable balloon inside said compartment, and
    a distal end of said body finishing in a head with a flexible neck through which said first internal channel extends, wherein the flexible neck is disposed on the proximal side of the head and a cross-sectional area perpendicular to an extending direction of the first internal channel in the flexible neck is smaller than the cross sectional area in the head.

2. The device for inserting an inflatable balloon, according to claim 1, wherein said first internal channel is arranged inside the main body along a central longitudinal axis of said body.

3. The device for inserting an inflatable balloon, according to claim 1, wherein said second internal channel is arranged along a longitudinal axis that is not concentric with a central axis of said body.

4. The device for inserting an inflatable balloon, according to claim 1, wherein said head is ogive shaped with a rounded point.

5. The device for inserting an inflatable balloon, according to claim 1, wherein said internal compartment comprises a truncated base along a longitudinal plane parallel to a central axis of the body and does not pass through the central axis of said main body.

6. The device for inserting an inflatable balloon, according to claim 1, wherein the distal end of said main body is more slender and more flexible than the proximal end of the body.

7. The device for inserting an inflatable balloon, according to either claim 1, wherein the length of said main body is less than the thread used to guide said device and less than the inflation tube of the inflatable balloon.

8. The device for inserting an inflatable balloon, according to claim 1, wherein the connection between the distal end of the inflation tube and the inflatable balloon is detachable.

9. The device for inserting an inflatable balloon, according to claim 1, wherein the inflatable balloon comprises a non return valve.

10. The device for inserting an inflatable balloon, according to claim 1, wherein the thread for guiding said device and the inflation tube of the inflatable balloon are of the flexible resilient type.

11. The device for inserting an inflatable balloon, according to claim 1, wherein said main body further comprises double length marking along the surface of said body to indicate the location of the head of the main body and the proximal end of the inflatable balloon during insertion of the device inside the patient.

12. A device for inserting an inflatable balloon that uses a thread for guidance comprising a main body of revolution which defines a cone shaped distal end and a proximal end, wherein said main body comprises:
    a first internal channel passing from the proximal end to the distal end of said body for inserting a thread for guiding said device;
    an internal compartment arranged in a portion of the distal end of said body for housing an inflatable balloon, said compartment comprising a breakable outer surface which is continuous with a surface of said body,
    a second internal channel passing from the proximal end of said body to said compartment, for housing an inflatable balloon inflation tube;

a distal end of said body finishing in a head with a flexible neck through which said first internal channel extends, and a resilient longitudinal opening for access to said second internal channel, arranged between the proximal end of said body and the compartment, for inserting a balloon inflation tube together with an inflatable balloon, wherein the flexible neck is disposed on the proximal side of the head and a cross sectional area perpendicular to an extending direction of the first internal channel in the flexible neck is smaller than the cross sectional area in the head.

13. The device for inserting an inflatable balloon, according to claim 12, wherein said first internal channel is arranged inside the main body along a central longitudinal axis of said body.

14. The device for inserting an inflatable balloon, according to claim 12, wherein said second internal channel is arranged along a longitudinal axis that is not concentric with a central axis of said body.

15. The device for inserting an inflatable balloon, according to claim 12, wherein said head is ogive shaped with a rounded point.

16. The device for inserting an inflatable balloon, according to claim 12, wherein said internal compartment comprises a base truncated along a longitudinal plane parallel to a central axis of the body and does not pass through the centre of said main body.

17. The device for inserting an inflatable balloon, according to claim 12, wherein the distal end of said main body is more slender and more flexible than the proximal end of the body.

* * * * *